United States Patent [19]

Rebsdat et al.

[11] 4,051,068

[45] Sept. 27, 1977

[54] PROCESS FOR REACTIVATING SILVER CATALYSTS USED IN THE MANUFACTURE OF ETHYLENE OXIDE BY DIRECT OXIDATION

[75] Inventors: Siegfried Rebsdat, Winhoring, Burg; Sigmund Mayer, Burgkirchen-Holzen; Josef Alfranseder, Hofschallern, all of Germany

[73] Assignee: Hoechst Aktiengesellschaft, Germany

[21] Appl. No.: 680,778

[22] Filed: Apr. 27, 1976

[30] Foreign Application Priority Data

May 2, 1975 Germany .............................. 2519599
Mar. 20, 1976 Germany .............................. 2611856

[51] Int. Cl.² ..................... B01J 23/96; C07D 301/10; C07D 303/04
[52] U.S. Cl. .................................. 252/412; 252/414; 260/348.23
[58] Field of Search ............... 252/411, 412, 414, 476; 260/348.5 R

[56] References Cited

U.S. PATENT DOCUMENTS

| | | | |
|---|---|---|---|
| 2,615,899 | 10/1952 | Sears, Jr. | 260/348.5 |
| 2,687,380 | 8/1954 | Saffer | 252/411 R |
| 3,899,445 | 8/1975 | Kajimoto et al. | 252/476 |
| 3,962,136 | 6/1976 | Nielson | 252/476 |

Primary Examiner—Winston A. Douglas
Assistant Examiner—P. E. Konopka
Attorney, Agent, or Firm—Connolly and Hutz

[57] ABSTRACT

The efficiency of silver carrier catalysts having reduced activity for the manufacture of ethylene oxide by reacting ethylene with oxygen or air is improved by impregnating the used catalyst with a solution containing cesium and/or rubidium compounds, an aliphatic alcohol and at most 10% by weight of water. After impregnation the alcohol and optionally the water are evaporated. The cesium and/or rubidium content of the impregnating solution and the number of impregnations are adjusted to obtain on the carrier a cesium and/or rubidium concentration of from 1 to 1,000 ppm.

9 Claims, 1 Drawing Figure

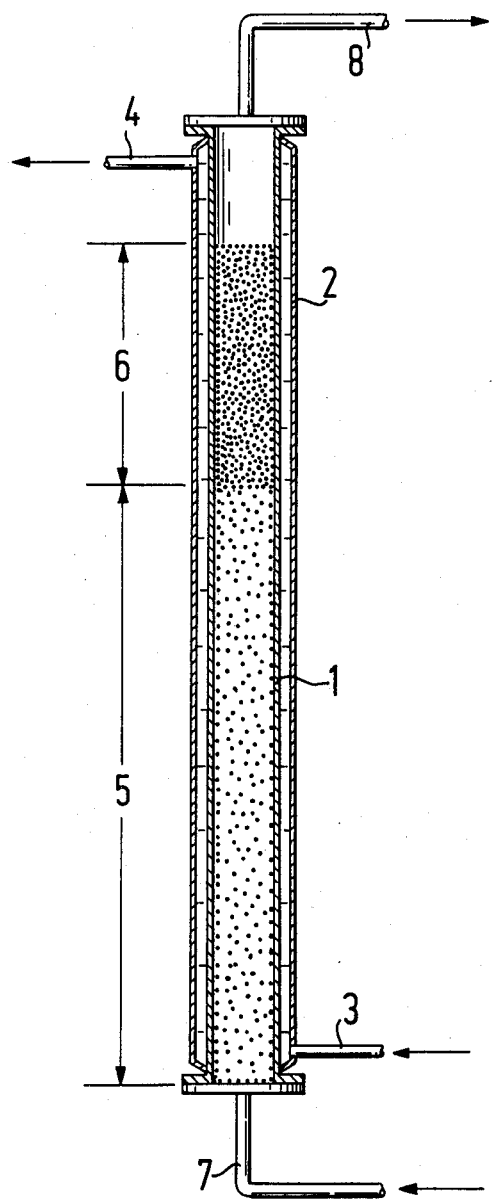

PROCESS FOR REACTIVATING SILVER CATALYSTS USED IN THE MANUFACTURE OF ETHYLENE OXIDE BY DIRECT OXIDATION

This invention relates to the reactivation of silver catalysts used in the manufacture of ethylene oxide by direct oxidation.

To produce ethylene oxide by oxidation of ethylene with oxygen silver catalysts are used, the preparation of which is known for a long time and described in numerous literature references. Quite a number of industrial plants for the manufacture of ethylene oxide make use of the silver catalyst process. In this process, ethylene is reacted with oxygen, in contact with a carrier material containing silver, to yield a preponderant proportion of ethylene oxide, while another noteworthy proportion is burned in a secondary reaction to carbon dioxide and water.

In the course of time most different silver catalysts have been developed with the aim to improve the selectivity with regard to the preferred formation of ethylene oxide and to suppress the formation of $CO_2$ and water.

With increasing costs for raw material and growing scarcity thereof an improvement of the catalyst selectivity is of considerable economic importance. In the last years it has been possible to develop silver catalysts having a selectivity of up to 75% of ethylene oxide as compared to older types having a selectivity of 65 to 70% only. Catalysts of this type are described, for example in German Offenlegungsschrift 2,300,512. They are obtained by applying to an inert carrier material, for example $Al_2O_3$, silver and simultaneously an aqueous solution of 0.00035 to 0.0030 g-equivalent of potassium, rubidium and/or cesium ions per kilogram of catalyst.

It is known that the selectivity of silver catalysts diminishes during the course of time and that after several years the catalysts must be replaced by fresh ones. The exchange of an exhausted catalyst for a fresh one in a large scale industrial plant is, apart from the material costs, very time consuming and requires much labor, the production must be interrupted and high expenses are involved. It is, therefore, desirable to improve the selectivity of exhausted catalysts by a simple treatment in order to avoid or delay as long as possible the exchange for a fresh catalyst. Up to now, such a treatment has not been proposed.

All processes described in this field exclusively relate, inclusive of the process of the aforesaid German Offenlegungsschrift, to the manufacture of novel improved catalysts.

The process of the present invention substantially differs from all known processes. It does not relate to the manufacture of a novel catalyst, but is concerned with the increase in activity of finished and already used catalysts which are at least partially deactivated, and this independent of their mode of preparation. The reactivation of aged catalysts in use in industrial plants is particularly advantageous.

It has now been found that the selectivity of used catalysts can be decisively improved by treating them with a solution of cesium and/or rubidium compounds in an aliphatic alcohol having from 1 to 6 carbon atoms, optionally with the addition of water in a proportion not exceeding a certain value. By this treatment the selectivity of the catalysts with regard to the preferred formation of ethylene oxide is improved to such an extent that it comes near to the selectivity of highly active fresh catalysts of the type described above.

The present invention therefore provides a process for reactivating silver carrier catalysts having a reduced activity, for the manufacture of ethylene oxide by reacting ethylene with molecular oxygen or air, which comprises adjusting on the catalyst a cesium and/or rubidium concentration of from 1 to 1,000 ppm by impregnating the said catalyst with a solution comprising cesium and/or rubidium compounds in an aliphatic alcohol having from 1 to 6 carbon atoms and containing at most 10% by weight of water and evaporating the alcohol and optionally the water, if any.

The aforesaid cesium and rubidium concentration on the catalyst relates to the cesium and rubidium cation, the anion of the compound used is not taken into consideration.

Suitable cesium and rubidium compounds are, for example, the nitrates, hydroxides, carbonates, acetates, chlorides, bromides, formates, propionates and oxalates, preferably the nitrates. The anion is obviously not critical, the reactivation is brought about by the cesium or rubidium cation. The use of salts or hydroxides proved to be particularly suitable.

In general, the cesium and/or rubidium compound is first dissolved in water and the aqueous solution obtained is added to an aliphatic alcohol having from 1 to 6 carbon atoms whereby a limpid solution is obtained. Preferred alcohols are methanol, ethanol, propanol and isopropanol, methanol being particularly suitable owing to its low boiling point and low price. The proportion of water in the impregnating solution is of decisive importance. It should not exceed 10% by weight of the total solution. If the cesium or rubidium compound to be used dissolves in the alcohol without the addition of water, the use of the latter can be dispensed with. In many cases, however, the use of water, which acts solely as dissolving intermediary, is necessary. In this case the cesium or rubidium compound is expediently dissolved in the minimum quantity of water required for complete dissolution and the solution obtained is diluted with the alcohol in an amount such that the final impregnating solution has a water content of at most 10% by weight.

A water content of from 0.2 to 5% by weight is preferred, especially in the case of cesium nitrate or rubidium nitrate. The concentration of the cesium and rubidium compound in the impregnating solution is limited by the solubility of the respective compound and it is not critical. In general, a minimum concentration of 0.01% by weight is recommended. A concentration in the range of from 0.05 to 0.4% by weight, calculated on the total solution, proved to be especially suitable. The concentration of the impregnating solution is defined, however, by the desired cesium and rubidium concentration on the catalyst.

A process of this type has neither been known nor has it been suggested by German Offenlegungsschrift No. 2,300,512, which exclusively discloses the manufacture of fresh catalysts and is suitable for this purpose only. Apart from this fact, in said reference it is expressly stated that silver and the promotor should be applied to the carrier material simultaneously In accordance with the recognized state of the art water is used as solvent in the reference process, while in the present process use is made of an aliphatic alcohol, if necessary or desired with the addition of a very limited amount of water. This is a critical feature of the process of the invention.

When purely aqueous solutions are used, the conversion of ethylene to ethylene oxide diminishes to 10 to 30% of the value reached prior to the treatment.

The catalyst can be treated with the impregnating solution in very simple manner by soaking it and decanting the excess solution. In an industrial plant the reactor containing the catalyst is flooded with the solution of the cesium or rubidium compound. After separation of the solution in excess, the alcohol and optionally water, if any, remaining on the catalyst is or are removed by evaporation, if desired while blowing through nitrogen. The temperature of evaporation is not critical, in general it will be somewhat above the boiling point of the alcohol used. When the treatment is carried out in a vacuum, the evaporation can even take place at room temperature or at 50° C, for example. In many cases, it is more advisable to choose higher temperatures, for example in the range of from about 50° to 180° C. With the use of methanol, ethanol, propanol, or isopropanol a temperature range of from 70° to 120° C, more preferably from 90° to 110° C proved to be advantageous. Also at these elevated temperatures the evaporation can be effected at reduced pressure. Whether or not the water possibly contained in the impregnating solution is evaporated together with the alcohol is without importance.

According to a preferred embodiment of the present invention, the used catalyst is impregnated with a solution consisting of 0.2 to 5% by weight of water, 0.05 to 0.4% by weight of cesium or rubidium nitrate and an aliphatic alcohol having from 1 to 3 carbon atoms and the alcohol is then evaporated at 70° to 120° C, preferably 90° to 110° C, optionally while blowing through nitrogen. For this purpose, the cesium nitrate or rubidium nitrate is first dissolved in the minimum quantity of water required for complete dissolution and the solution obtained is diluted with methanol, ethanol, propanol, or isopropanol, preferably methanol, in an amount such that the final impregnating solution has a water concentration of from 0.2 to 5% by weight. The concentration of rubidium nitrate or cesium nitrate in the solution is in the range of from 0.05 to 0.4% by weight, calculated on the total solution. The concentration of rubidium or cesium on the catalyst is in the range of from 2 to 1,000 ppm, preferably 3 to 500 ppm and more preferably 10 to 300 ppm, which can be adjusted by a corresponding concentration of the impregnating solution.

The following table shows that the selectivity of a catalyst with reduced activity can be considerably improved by the treatment according to the invention. Moreover, the conversion is doubled or even tripled or with the same degree of conversion the reaction temperature can be reduced by 20° to 30° C.

|  | Selectivity at 230° C | Conversion at 245° C | Conversion at 220° C |
|---|---|---|---|
| prior to treatment | 68 – 70% | 4 – 5% | — |
| after treatment | 73 – 78% | 10 – 12% | 4 – 5% |

The possibility to reduce the reaction temperature constitures a further advantage of the process of the invention since the formation of undesired secondary products, such as $CO_2$, formaldehyde and acetaldehyde, diminishes with decreasing temperature. In this manner the ethylene oxide obtained has a higher degree of purity and the danger of corrosion is reduced.

The treatment according to the invention is useful only for catalysts the activity of which has diminished during operation.

A further advantage of the process of the invention resides in the fact that it may be adapted to the requirement of the respective plant. In many cases the change to a catalyst of higher selectivity with increased yield and conversion rate is only possible with considerable investment as the dimensions of the apparatus for the dissipation of heat and working up the reaction mixture now having a much higher content of ethylene oxide are too small. According to the invention a just possible or desired increase in the conversion can be adjusted by an exact dosage of the applied cesium or rubidium compound.

The following examples illustrate the invention. The experiments were continued for a period of time such that no more changes of the results were observed. In a subsequent longtime test lasting 200 hours the results could be reproduced. The products were analyzed by gas chromatography. The indicated data of conversion and selectivity are average values of a series of measurements.

To test the efficiency of the catalyst treated according to the invention a reactor was used as shown, by way of example, in the accompanying drawing and consisting of a reaction tube 1 of chrome vanadium steel having an inside diameter of 30 mm and a length of 800 mm. The reaction tube 1 was heated by means of a jacket 2 with circulating oil supplied through inlet 3 and discharged through outlet 4. Zone 5 of the reaction tube (length 500 mm) was filled with $\alpha\text{-}Al_2O_3$ and served to preheat the feed gas. Zone 6 of the reaction tube 1 (length 200 mm) contained the catalyst. The feed gas was supplied through conduit 7 and left the reaction tube 1 through conduit 8. As inhibitor 1 to 3 ppm of vinyl chloride were added to the feed gas.

The gas mixture used consisted of

25% of $C_2H_4$
50% of $CH_4$
8% of $O_2$
17% of inert gas ($N_2$).

COMPARATIVE EXAMPLE 1

In the reaction tube as described above 70 g of a commercial silver catalyst (carrier material $\alpha\text{-}Al_2O_3$, silver content 11.3%), which had been used for 7 years in a large scale industrial plant, were tested under the following conditions:

space-time velocity: 250 /hr
(parts by volume gas,
per part by volume catalyst.hr)
pressure: 1 atmosphere.

To obtain a conversion of 5% a temperature of 240° C was required. The selectivity amounted to 70.5%.

EXAMPLE 1

0.2 g of cesium nitrate (pure) was dissolved in 0.5 g of distilled water and an impregnating solution was prepared by adding while stirring the solution obtained to 100 cc of methanol (technical grade).

70 g of catalyst (as in comparative Example 1) were introduced into a vertical tube having an inside diameter of 20 mm and the impregnating solution was poured thereover. The excess solution flowing off at the lower end of the tube was recollected and poured again into the tube at the upper end. In this manner, the catalyst was treated five times. 10 ml of impregnating solution remained on the catalyst. The impregnated catalyst was dried for 1 hour at 110° to 130° C in a drying cabinet. From the applied amount of impregnating solution a cesium content of the treated catalyst of 200 ppm was calculated.

The impregnated catalyst was introduced into the reaction tube as described in comparative Example 1 and contacted with the feed gas under the conditions specified in said example space-time velocity: 250/hr
pressure: 1 atmosphere
temperature: 240° C.

With a conversion of 7% the selectivity amounted to 75%. When the temperature was reduced to 230° C, the selectivity obtained was 77% with a conversion rate of 5%.

COMPARATIVE EXAMPLE 2

The experiment of Example 1 was repeated with the exception that methanol in which no cesium compound had been dissolved was used.

space-time velocity: 250/hr
pressure: 1 atmosphere
temperature: 240° C.

The selectivity amounted to 71% with a conversion rate of 5%.

EXAMPLES 2 to 16

The experiments were carried out as described in Example 1 under varying reaction conditions as defined in the following Table 1.

EXAMPLE 17

The experiment of Example 1 was repeated with the exception that ethanol was used instead of methanol, the reaction temperature was 240° C and the cesium concentration on the catalyst 80 ppm.

space-time velocity: 250 /hr
pressure: 1 atmosphere
temperature: 240° C.

With a conversion rate of 5% the selectivity amounted to 76%.

COMPARATIVE EXAMPLE 3

The experiment of Example 1 was repeated with the exception that water was used instead of methanol.

With the use of the catalyst (as in comparative Example 1) treated with the aqueous solution a conversion of 0.8% only was obtained at 240° C. As compared with the untreated catalyst, the catalyst was strongly damaged and unsuitable for the further production of ethylene oxide.

TABLE 1

| Example | alkali metal content of catalyst | space-time velocity | temperature ° C | selectivity % | $C_2H_4$-conversion % |
|---|---|---|---|---|---|
| Comp. Ex. 1 | 0 (untreated) | 250 | 240 | 70 - 70.5 | 5 |
| 1 | 200 ppm Cs | 250 | 240 | 75 | 7 |
| Comp. Ex. 2 | 0 (treated with methanol only) | 250 | 240 | 71 | 5 |
| 2 | 200 ppm Cs | 250 | 230 | 77 | 5 |
| 3 | 120 ppm CS | 250 | 230 | 76 | 8 |
| 4 | 120 ppm CS | 250 | 220 | 76.5 | 5 |
| 5 | 80 ppm CS | 720 | 250 | 73.5 | 6 |
| 6 | 80 ppm CS | 250 | 240 | 74 | 12 |
| 7 | 80 ppm CS | 250 | 230 | 77 | 7 |
| 8 | 80 ppm Cs | 200 | 220 | 78 | 5 |
| 9 | 45 ppm Cs | 1800 | 260 | 73 | 6 |
| 10 | 45 ppm Cs | 500 | 250 | 75 | 6 |
| 11 | 45 ppm Cs | 250 | 240 | 77 | 7 |
| 12 | 45 ppm Cs | 230 | 230 | 77.5 | 5 |
| 13 | 45 ppm Cs | 140 | 220 | 78 | 4.5 |
| 14 | 30 ppm Cs | 250 | 230 | 76 | 5 |
| 15 | 15 ppm Cs | 250 | 240 | 74 | 5 |
| 16 | 50 ppm Rb | 250 | 240 | 74.5 | 5 |
| 17 | 80 ppm Cs | 250 | 240 | 76 | 5 |
| Comp. Ex. 3 | 200 ppm Cs | (aqueous solution) 250 | 240 | — | 0.8 |

EXAMPLE 18

0.061 g of cesium hydroxide ($CsOH.H_2O$) was dissolved in 0.5 g distilled water and an impregnating solution was prepared by stirring the solution obtained into 100 cc of methanol (technical grade). 70 g of catalyst (as in comparative Example 1) were introduced into a vertical tube having an inside diameter of 20 mm and the impregnating solution was poured thereover. The excess solution flowing off at the lower end of the tube was recollected and poured again over the catalyst. The catalyst was treated in this manner five times and 10 ml of the impregnating solution remained thereon. The impregnated catalyst was dried for one hour at 110° to 130° C in a drying cabinet. From the applied amount of impregnating solution a cesium content of the treated catalyst of 110 ppm was calculated.

The impregnated catalyst was introduced into the apparatus described above and contacted with the feed gas at a temperature of 230° C, a pressure of 1 atmosphere and a space-time velocity of 250/hr (parts by volume of gas per part by volume of catalyst.hr). With a conversion rate of 5% a selectivity of 76% was obtained.

EXAMPLE 19

An impregnating solution was prepared from 0.0604 g of cesium carbonate and 100 cc of methanol and the catalyst was treated with the solution under the conditions of Example 18. The impregnated catalyst had a cesium content of 100 ppm.

Under the conditions of Example 18, there was obtained a conversion of 5.5% and a selectivity of 76% at a temperature of 230° C.

EXAMPLE 20

The experiment was carried out under the conditions of Example 18 using an impregnating solution consisting of 0.0324 g of cesium acetate, 0.5 g of distilled water and 100 cc of methanol. The impregnated catalyst contained 80 ppm of cesium.

At a temperature of 230° C, a conversion rate of 6% and a selectivity of 75.5% were obtained.

What is claimed is:

1. Process for reactivating used silver carrier catalysts for the manufacture of ethylene oxide by reacting ethylene with molecular oxygen or air, which comprises adjusting on the catalyst a concentration of cesium, rubidium or of both of from 1 to 1,000 ppm by impregnating the said catalyst with a solution of cesium, rubidium or of both compounds selected from the group consisting of salts and hydroxides in an aliphatic alcohol having from 1 to 6 carbon atoms and containing at most 10% by weight of water and evaporating the alcohol and any water present.

2. Process for improving the efficiency of used silver catalysts for the manufacture of ethylene oxide by reacting ethylene with molecular oxygen or air, which comprises adjusting on the catalyst a concentration of cesium, rubidium or of both of from 1 to 1,000 ppm by
   1. 0.2 to 5% by weight of water
   2. 0.05 to 0.4% by weight of cesium or rubidium nitrate and
   3. an aliphatic alcohol having from 1 to 3 carbon atoms, and evaporating the alcohol at a temperature of from 70° to 120° C.

3. The process of claim 1, wherein the aliphatic alcohol is methanol.

4. The process of claim 2, wherein the aliphatic alcohol is methanol.

5. The process of claim 1, wherein said concentration of from 3 to 500 ppm is adjusted on the catalyst.

6. The process of claim 1, wherein said concentration of from 10 to 300 ppm is adjusted on the catalyst.

7. The process of claim 2, wherein said concentration of from 3 to 500 ppm is adjusted on the catalyst.

8. The process of claim 2, wherein said concentration of from 10 to 300 ppm is adjusted on the catalyst.

9. Process of claim 2 wherein nitrogen is blown through during said evaporation.

* * * * *